United States Patent [19]

Pein et al.

[11] Patent Number: 4,933,459
[45] Date of Patent: Jun. 12, 1990

[54] PHARMACEUTICALS CONTAINING ACYLATED BENZILIC ACID DERIVATIVES FOR INFLUENCING THE TONE OF THE URINARY BLADDER

[75] Inventors: Eckhart Pein, Northeim; Helmut Ritter, Wuppertal; Reinhard Laven, Salzgitter, all of Fed. Rep. of Germany

[73] Assignee: Schaper & Bruemmer GmbH & Co., KG, Salzgitter, Fed. Rep. of Germany

[21] Appl. No.: 285,171

[22] Filed: Dec. 16, 1988

[30] Foreign Application Priority Data

Dec. 16, 1987 [DE] Fed. Rep. of Germany ....... 3742580

[51] Int. Cl.$^5$ .......................................... C07D 211/44
[52] U.S. Cl. .................................... 546/217; 546/195; 546/216; 546/218
[58] Field of Search ............... 546/216, 217, 218, 195

[56] References Cited

U.S. PATENT DOCUMENTS

| | | | |
|---|---|---|---|
| 2,955,114 | 10/1960 | Biel | 546/216 |
| 3,031,456 | 4/1962 | Holysz | 546/217 |
| 4,482,561 | 11/1984 | Nardi et al. | 546/218 |
| 4,855,307 | 8/1989 | Perregaard | 546/218 |

Primary Examiner—Glennon H. Hollrah
Assistant Examiner—Ba K. Trinh
Attorney, Agent, or Firm—Foley & Lardner, Schwartz, Jeffery, Schwaab, Mack, Blumenthal & Evans

[57] ABSTRACT

Certain acylated benzilic acid derivatives are useful for influencing therapeutically the tone of the urinary bladder in humans and animals. These derivatives are N-alkyl-4-piperidyl α,α-diphenyl-α-acyloxyacetates having the formula

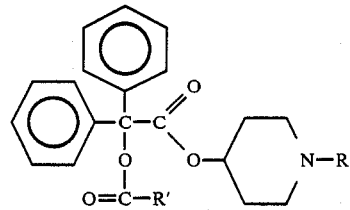

(I)

wherein R is H, $CH_3$, $C_2H_5$ or $C_3H_7$; R' is H, $NH_2$, phenyl, carboxyphenyl, ($C_1$-$C_6$)alkyl, hydroxy($C_1$-$C_6$)alkyl, methoxy, ethoxy, methoxymethyl, ethoxymethyl, amino ($C_1$-$C_6$)alkyl which can be substituted in the alkyl radical by one or more of a —$NH_2$, —COOH or —$SCH_3$ group, N-acetylamino ($C_1$-$C_6$)alkyl, or a group having the formula —CH=CH—COOR" or —$(CH_2)_n$—COOR"

where n is an integer from 0 to 8, and R" is H, $CH_3$, $C_2H_5$, $C_3H_7$, or a pharmacologically acceptable cation; or a salt thereof with a pharmaceutically acceptable acid.

7 Claims, 3 Drawing Sheets

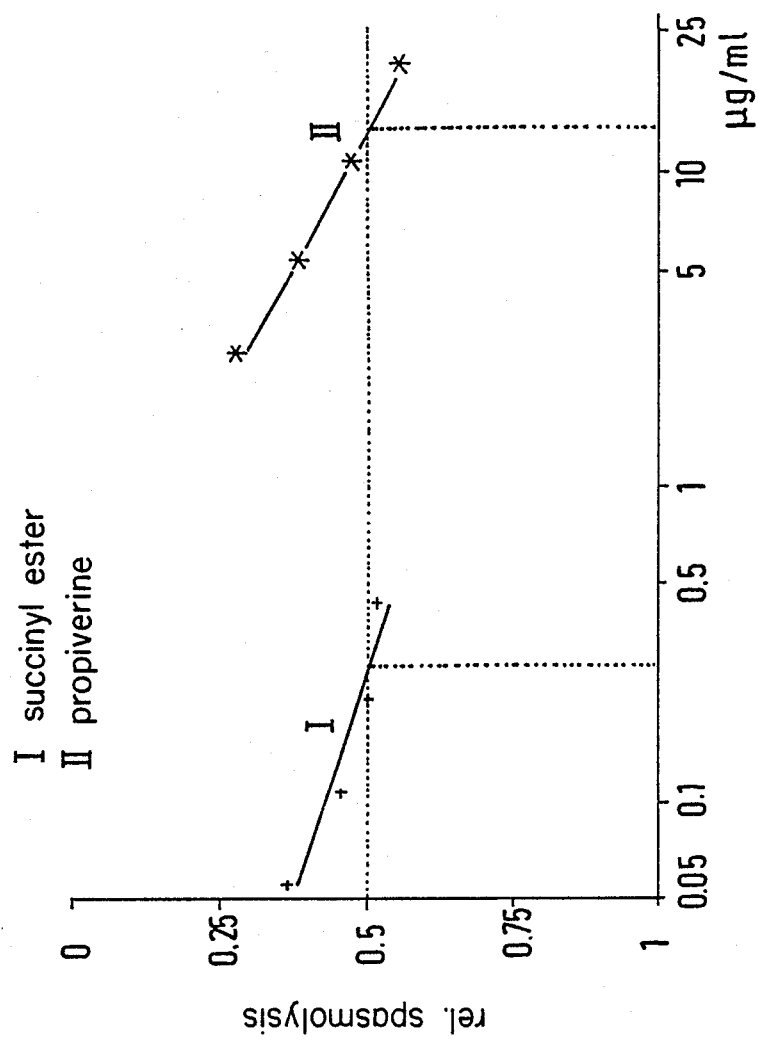

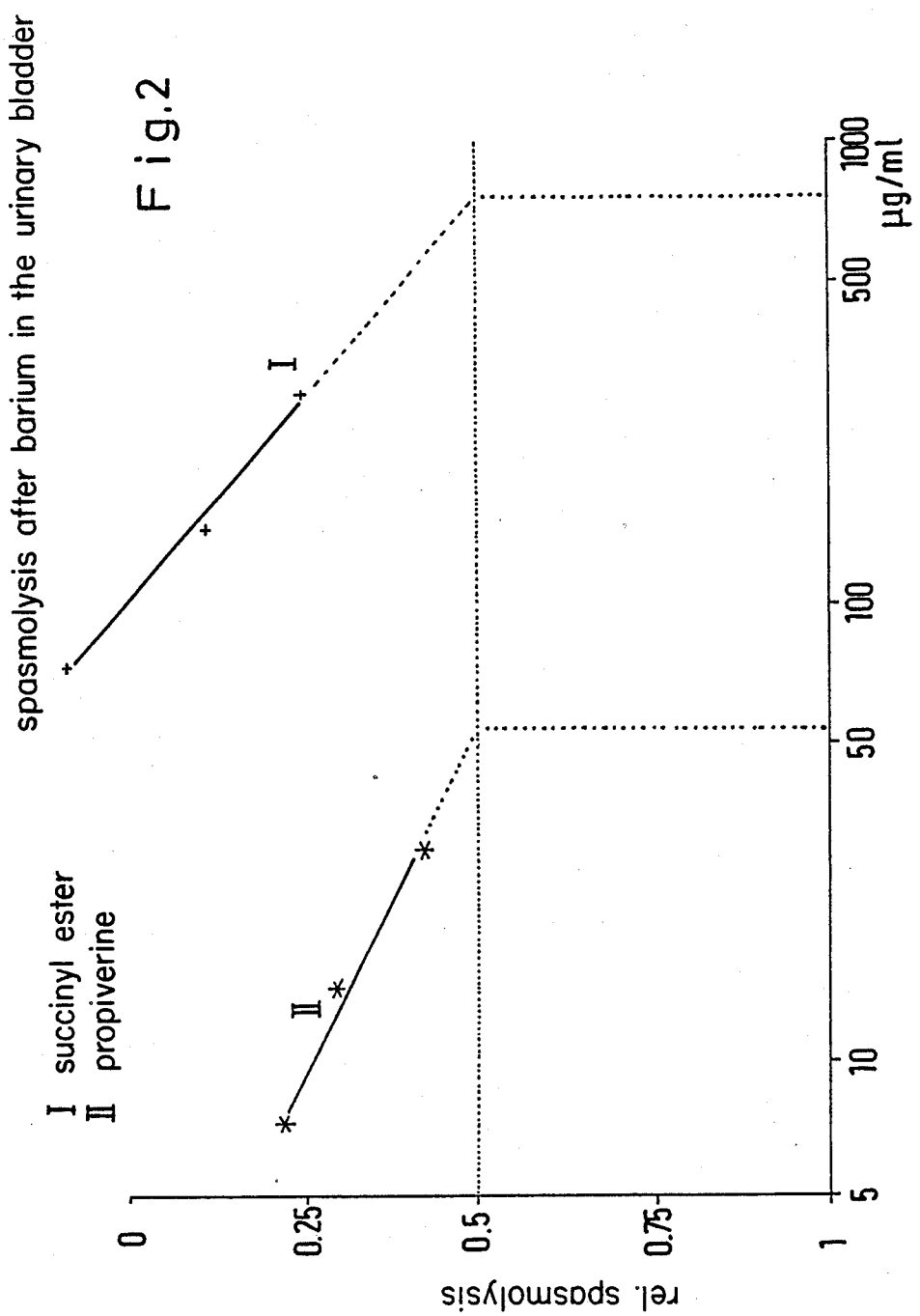

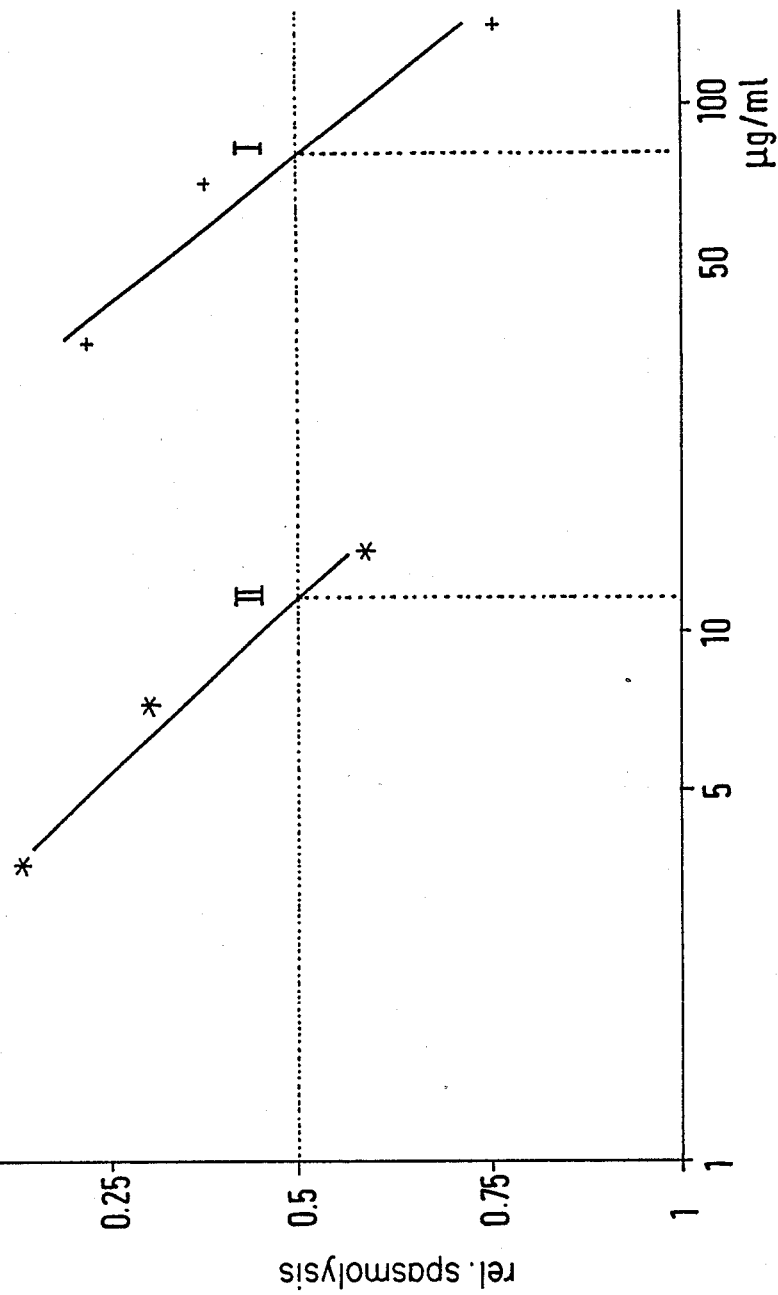

PHARMACEUTICALS CONTAINING ACYLATED BENZILIC ACID DERIVATIVES FOR INFLUENCING THE TONE OF THE URINARY BLADDER

BACKGROUND OF THE INVENTION

The present invention relates to the use of acylated benzilic acid derivatives in the form of N-alkyl-4-piperidyl α,α-diphenyl-α-acyloxyacetates for therapeutic purposes. It also relates to novel benzilic acid derivatives.

Numerous substances which are based on α,α-diphenylacetic acids and which have found use in pharmacotherapy as neurotropic or myotropic spasmolytics have been described. However, a selective effect of these substances specifically on the tone of the urinary bladder has not hitherto been satisfactorily demonstrated. Only the etherified derivative propiverine (1-methyl-4-piperidyl α,α-diphenyl-α-(n-propoxy)acetate) has shown therapeutic utility for this purpose (Zbl. Pharm. 120 (1981), 12, pages 1219-1224). However, this compound is insufficiently effective in some patients and is not amenable to general use because of certain side effects. Moreover, the hydrophobic nature of the compound results in diminished selectivity in the target area of the urinary bladder.

Furthermore, the large intrinsic myotropic/spasmolytic effect of parasympatholytic compounds hitherto used not uncommonly brings about inadequate contraction of the bladder muscle in the urinary bladder on active micturition, with the risk of the formation of residual urine.

The lowering of the blood pressure as has been described for therapy with propiverine (M. Blau, U. Retzke, Zbl. Gynakol. 100 (1984), 14, pages 981-987) may be regarded as another disadvantage of a pronounced myotropic/spasmolytic activity.

OBJECTS OF THE INVENTION

One object of the present invention is to provide pharmaceutical preparations which do not have the described disadvantages and are suitable for selective therapy of hypertonic functional states of the urinary bladder.

Another object of the invention is to provide novel acylated benzilic acid derivatives.

A further object of the invention is to provide a method of treating hypertonic functional states of the urinary bladder.

BRIEF DESCRIPTION OF THE DRAWINGS

FIGS. 1 and 2 are plots of the spasmolytic activities of a compound according to the invention and a prior art compound, in a guinea pig urinary bladder muscle model.

FIG. 3 is a plot of the spasmolytic activities of the same two compounds, in a guinea pig taenia coli model.

SUMMARY OF THE INVENTION

The foregoing objects are achieved according to the invention by providing a pharmaceutical preparation containing acylated benzilic acid derivatives having the formula

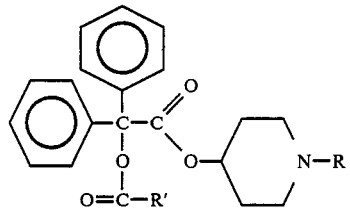

(I)

wherein R is H, $CH_3$, $C_2H_5$ or $C_3H_7$; R' is H, $NH_2$, phenyl, carboxyphenyl, $(C_1-C_6)$alkyl, hydroxy$(C_1-C_6)$alkyl, methoxy, ethoxy, methoxymethyl, ethoxymethyl, amino$(C_1-C_6)$alkyl which can be substituted in the alkyl radical by one or more of a $-NH_2$, $-COOH$ or $-SCH_3$ group, N-acetylamino$(C_1-C_6)$alkyl, or a group having the formula $-CH=CH-COOR''$ or $-(CH_2)_n-COOR''$ where n is an integer from 0 to 8; and R'' is H, $CH_3$, $C_2H_5$, $C_3H_7$, or a pharmacologically acceptable cation; or a salt thereof with a pharmacologically acceptable acid.

Preferably, the preparation comprises an amount effective for therapy of hypertonic functional states in the human or animal urinary bladder of at least one compound of formula I, together with a pharmaceutically acceptable vehicle. The invention also provides a method for treating hypertonic functional states in the urinary bladder of a human or an animal.

DETAILED DESCRIPTION OF THE PREFERRED EMBODIMENTS

Preferred compounds of formula I include those wherein R is $CH_3$; and those wherein R' is $-CH=CH-COOR''$ or $-(CH_2)_n-COOR''$, and n is an integer from 0 to 5, and particularly preferably 2. When n is 0, then R' is a $-COOR''$ group wherein R'' is as defined above.

Particularly preferred compounds are those in which R' denotes the group $-(CH_2)_n-COOR''$, wherein n=1 and, in particular, 2 or 3, and R'' is as defined above. In the latter case, R'' preferably represents a hydrogen atom or a pharmacologically acceptable cation. Also preferred are those compounds in which R' is $CH_3$ or $C_2H_5$.

Particularly suitable within the scope of the present invention are the compounds N-methyl-4-piperidyl α,α-diphenyl-α-(3-carboxypropionyloxy)acetate and N-methyl-4-piperidyl α,α-diphenyl-α-(4-carboxybutyryloxy)acetate (hereinafter also referred to by the abbreviated terms "succinyl ester" and "glutaryl ester", respectively), as well as the salts thereof with pharmacologically acceptable acids. These compounds have the formula I, wherein R is a methyl group, and R' is $-(CH_2)_2-COOR''$ or $-(CH_2)_3-COOR''$ (R''=H). These compounds normally exist in the betaine form, i.e., the form wherein the carboxyl group is in the form of a carboxylate anion and the piperidine ring nitrogen is protonated to form a piperidinium cation. However, they are also active in the form of esters (e.g., R''=$CH_3$, $C_2H_5$ or $C_3H_7$), or salts (R''=a pharmacologically tolerated cation). They can also be used as acid addition salts as defined hereinafter (in which case R'' is preferably H, $CH_3$, $C_2H_5$ or $C_3H_7$).

The compounds used in compositions according to the invention can be in the form of free bases, in the betaine form when a carboxyl substituent is present, e.g., when the radical R'' in the group $-(CH_2$ )$_n$—COOR" is an H atom, or in the form of acid addition salts thereof with pharmacologically acceptable acids. Examples of such acids are inorganic acids, e.g., hydrochloric acid, sulfuric acid and the like, or organic acids, e.g., acetic acid, propionic acid, citric acid and the like, and also including polymeric acids, e.g., carboxymethylcellulose.

The compounds used according to the invention, and especially the above-mentioned preferred derivatives, are particularly suitable for the drug therapy of hypertonic functional states in the urinary bladder owing to selective inhibition of micturition frequencies which are under parasympathetic control. It is possible in this way to treat pathological states such as irritable bladder with hyperreflexia after irradiation and associated with chronic cystitis. Further indications are urge incontinence, pollakiuria and nycturia. The low myotropic/-spasmolytic activity of the succinyl ester which is preferably used appears to be particularly advantageous from the therapeutic viewpoint.

The acylated benzilic acid derivatives of the general formula I in which R' is —(CH$_2$)$_n$—COOR" are novel. The invention thus also relates to novel N-alkyl-4-piperidyl α,α-diphenyl-α-acyloxyacetates of the general formula Ia

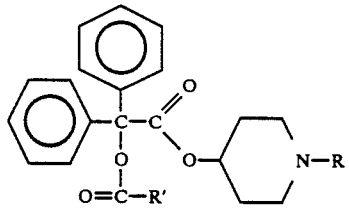

(Ia)

wherein R is H, CH$_3$, C$_2$H$_5$ or C$_3$H$_7$, and R' is

—(CH$_2$)$_n$—COOR"

where n is an integer from 0 to 8, preferably 0 to 5, more preferably 1 to 3, and particularly preferably 2 or 3, and R" is H, CH$_3$, C$_2$H$_5$, C$_3$H$_7$ or a pharmacologically tolerated cation such as an alkali metal (e.g., Li, Na or K), Ca, Al or ammonium ion; and acid addition salts thereof with pharmacologically tolerated acids, e.g., those exemplified above.

The radical R in the above-mentioned formula Ia is preferably a methyl group. Preferred derivatives are those in which n=2 or 3. Also preferred are the derivatives which are indicated above as preferred for therapeutic use for improving the tone of the urinary bladder, and are embraced by the general formula Ia, as well as the salts thereof. Particularly preferred are the above-mentioned succinyl and glutaryl esters and the salts thereof with pharmacologically tolerated acids.

The compounds according to the invention, and the pharmaceutical compositions according to the invention, and the salts thereof, are prepared by O-acylation of N-alkyl-4-piperidyl α,α-diphenyl-α-hydroxyacetates with suitable organic acids or the activated derivatives thereof. Examples of suitable activated derivatives are diacid chlorides or cyclic anhydrides or alkyl diesters of carbonic acid. A free functional group or COOH group which is obtained is, where appropriate, converted in a customary manner into the desired form, e.g., esterified with an appropriate alcohol or converted into the desired salt. The α-hydroxy esters can be prepared by the method of J. Klosa and G. Delmar, J. fur prakt. Chemie, 4., vol. 16, pp. 71 et seq. (1962).

Examples of suitable acids for the O-acylation are:

(a) monofunctional carboxylic acids such as formic acid, acetic acid, propionic acid, butyric acid and benzoic acid, (b) hydroxy acids such as hydroxyacetic acid, lactic acid, hydroxybutyric acid, methoxyacetic acid and ethoxyacetic acid, (c) amino acids such as glycine, alanine, aspartic acid, methionine and lysine, or (d) difunctional acids or dicarboxylic acids where the carboxyl group which is not involved in the O-acylation can be in the form of the free acid, methyl, ethyl or propyl ester or in the form of a salt, e.g., an alkali metal (Li, Na or K), Ca, Al or ammonium salt. Examples of suitable dicarboxylic acids are oxalic acid, malonic acid, succinic acid, glutaric acid, adipic acid, sebacic acid, maleic acid or phthalic acid. Suitable difunctional acids include carbonic acid and carbamic acid. It is possible to use the acids, for example, in the form of activated derivatives thereof suitable for acylation, such as acyl halides, and the dicarboxylic acids in the form of their anhydrides.

The acylated benzilic acid derivatives can be administered in a variety of ways, e.g., by oral, intravenous or subcutaneous routes. They can be formulated in bulk or in convenient dosage forms, in the customary manner, e.g., in effective doses in the form of a powder (e.g., a capsule), or a tablet, or in aqueous or oily dispersion. The active agent can be used in combination with other therapeutic agents such as antibiotics, tranquilizers or analgesics. Customary formulation auxiliaries and additives maybe used for preparing the compositions according to the invention. The generally inert formulation auxiliaries and additives for any particular dosage form are herein denoted a "pharmaceutically acceptable vehicle" for that dosage form. Illustrative vehicles are shown in the examples.

Effective amounts of particular compounds of formula I, or mixtures thereof, can be determined by analogy to those already known in the art for the therapeutic use of propiverine in treating hypertonic functional states of the urinary bladder. This can be done by determination of the relative neurotropic/spasmolytic activity of the compound(s) according to the present invention compared to propiverine, using the guinea pig urinary bladder muscle model as illustrated in the examples. This will indicate the ratio of the present compound(s) compared to propiverine to be used in a single unit dose or in a course of therapy.

The examples which follow are intended to illustrate the invention but are not to be construed as limiting its scope.

EXAMPLE 1

Preparation of N-Methyl-4-piperidyl Benzilate Succinyl Ester 3.25 g of N-methyl-4-piperidyl benzilate and 1.1 g of succinic anhydride are refluxed in 50 ml of dioxane for 8 hours. The solvent is removed by distillation and the product is recrystallized from ethanol. Crystals of melting point 168° C. are obtained in a yield of 80%.

| Elemental analysis | | | |
| --- | --- | --- | --- |
| C | H | N | |
| 67.75 | 6.40 | 3.29 | (calculated) |
| 67.72 | 6.67 | 3.42 | (found) |

EXAMPLE 2

Formulation of Pharmaceutical Dosage Forms

| | |
| --- | --- |
| 1. 200 mg tablets | |
| Succinyl ester (N-methyl-4-piperidyl α,α-diphenyl-α-(3-carboxypropionyloxy)acetate) | 20 mg |
| Microcrystalline cellulose (Avicel pH 102 from Atlas Chemicals) | 159 mg |
| Crosslinked polyvinylpyrrolidone (Polyplasdone XL from Antara Chemicals) | 20 mg |
| Magnesium stearate | 1 mg |
| 2. 300 mg capsules | |
| Succinyl ester | 20 mg |
| Yellow beeswax | 10 mg |
| Soy bean oil | 10 mg |
| Vegetable oil | 160 mg |
| Capsule shell | 100 mg |
| 3. Injection ampoules | |
| Succinyl ester | 20 mg |
| Physiological NaCl | ad 2 ml |
| 4. Infusion solutions | |
| Succinyl ester | 2 g |
| Phys. NaCl | ad 500 ml |
| 5. Liquid oral drug form | |
| Succinyl ester | 500 mg |
| Sorbitol | 10 g |
| Saccharin sodium | 0.050 g |
| Thanol 20% (V/V) | ad 100 ml |
| Flavoring essence q.s. | |

In the examples which follow, the pharmacological activity of the preferred succinyl ester compound is demonstrated, which illustrates the utility of compositions according to the invention for the treatment of hypertonic functional disturbances of the smooth muscles of the urogenital system.

EXAMPLE 3

Activity of Succinyl Ester

The neurotropic/spasmolytic effect of the succinyl ester compared to propiverine is investigated in vitro on an isolated preparation of guinea pig urinary bladder muscle by customary techniques. The spasmodic agent used is carbachol. Carbachol is added in a dosage of 10 μg/ml to the organ bath in order to achieve maximum contraction of the muscle preparation.

The compounds to be tested are added, five minutes after activation of the muscle preparation by carbachol, in increasing dosage to the organ bath, and the corresponding $ED_{50}$ values are determined from the resulting dose-response plots.

It is found from these experiments that the succinyl ester has a pronounced, almost specific neurotropic/-spasmolytic activity which is distinctly higher, by a factor of 50, than that of propiverine (see FIG. 1).

EXAMPLE 4

Activity of Succinyl Ester

Again using the model of the isolated preparation of guinea-pig urinary bladder muscle, the myotropic/spasmolytic activities of the succinyl ester and propiverine are investigated and compared. The spasmodic agent used is barium chloride. Barium chloride is added in a dosage of 0.2 mg/ml to the organ bath to induce maximum contraction of the bladder muscle.

While the myotropic/spasmolytic activity of propiverine ($ED_{50}$ 53.05 μg/ml) reaches the potency of papaverine, the succinyl ester has a myotropic/spasmolytic activity which is weaker by a factor of 14 (see FIG. 2).

EXAMPLE 5

Related Activity of Succinyl Ester

For further confirmation of the findings, the myotropic/spasmolytic activities of propiverine and the succinyl ester are also determined in vitro in the isolated guinea pig taenia coli model.

The spasmodic agent used is barium chloride in a bath concentration of 0.2 mg/ml.

The $ED_{50}$ for propiverine is 12 μg/ml, and the $ED_{50}$ for the succinyl ester is 94 μg/ml, i.e., the succinyl ester also has a significantly lower myotropic/spasmolytic activity than propiverine in this experimental model (see FIG. 3).

EXAMPLE 6

Preparation of Glutaryl Ester

The procedure described in Example 1 is used, but succinic anhydride is replaced by glutaric anhydride. The resulting glutaryl ester, having formula Ia, wherein $R=CH_3$ and $R'=-(CH_2)_3-COOH$, shows in the IR spectrum (KBr) 2 ester peaks at 1725 and 1735 cm$^{-1}$ and one carboxylate peak at 1560 cm$^{-1}$.

EXAMPLE 7

Preparation of Acetyl Ester

The acetyl compound having the formula I in which $R=CH_3$ and $R'=CH_3$ is prepared as described by J. Klosa and G. Delamar in J. fur praktische Chemie, 4., vol. 16, pp. 71 et seq. (1962).

EXAMPLE 8

Comparative Activities

The neutrotropic/spasmolytic activities and the myotropic/spasmolytic activities of the compounds prepared according to Examples 1, 6 and 7, as well as of the comparison substance propiverine, are determined as described in Example 5. In a similar manner, experiments on isolated guinea pig ileum were carried out. The conditions and results are indicated in the Table which follows. It is evident that the neurotropic/spasmolytic effect predominates with the compounds according to the invention, while the undesired myotropic/spasmolytic effect predominates with the comparison compound.

TABLE

| | Neurotropic/myotropic/ spasmolytic activity | |
| --- | --- | --- |
| | Ileum Carbachol 50 ng/ml | Taenia coli Barium 200 μg/ml |
| Comparison (Propiverine) | 59 ng | 12 μg (EC 50) |
| Acetic ester (Ex. 7) | 5 ng | 76 μg (EC 50) |
| Succinic ester (Ex. 1) | 0.8 ng | 94 μg (EC 50) |
| Glutaric ester (Ex. 6) | 1.5 ng | 229 μg (EC 50) |

What is claimed is:

1. An N-alkyl-4-piperidyl α,α-diphenyl-α-acyloxyacetate having the formula

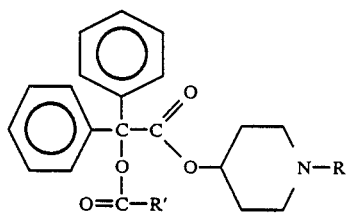
(Ia)

wherein R is H, CH$_3$, C$_2$H$_5$ or C$_3$H$_7$; and R' is

—(CH$_2$)$_n$—COOR'' where n is an integer from 0 to 8; and R'' is H, CH$_3$, C$_2$H$_5$, C$_3$H$_7$ or a pharmacologically acceptable cation; or a salt thereof with a pharmacologically acceptable acid.

2. The compound of claim 1, wherein n is an integer from 0 to 5.

3. The compound of claim 2, wherein n is an integer from 1 to 3.

4. The compound of claim 3, wherein n is 2.

5. The compound of claim 1, wherein R is CH$_3$.

6. N-Methyl-4-piperidyl α,α-diphenyl-α-(3-carboxypropionyloxy)acetate, and acid addition salts thereof with pharmacologically acceptable acids.

7. N-Methyl-4-piperidyl α,α-diphenyl-α-(4-carboxybutyryloxy)acetate, and acid addition salts thereof with pharmacologically acceptable acids.

* * * * *